United States Patent [19]
Amrein et al.

[11] Patent Number: 5,868,580
[45] Date of Patent: Feb. 9, 1999

[54] TRAINING DEVICE FOR DIGITAL ASSESSMENT OF INTRAOCULAR PRESSURE

[75] Inventors: Bruce E. Amrein, Bel Air; James W. Karesh, Chevy Chase, both of Md.

[73] Assignee: The United States of America as represented by the Secretary of the Army, Washington, D.C.

[21] Appl. No.: 903,337

[22] Filed: Jul. 30, 1997

[51] Int. Cl.⁶ .................................................. G09B 23/28
[52] U.S. Cl. .......................................................... 434/271
[58] Field of Search ................................... 434/271, 270, 434/267

[56] References Cited

U.S. PATENT DOCUMENTS

| | | | |
|---|---|---|---|
| 3,736,789 | 6/1973 | Drew | 73/1 B |
| 4,000,640 | 1/1977 | Kocmich | 73/1 B |
| 4,865,551 | 9/1989 | Maloney et al. | 434/271 |

FOREIGN PATENT DOCUMENTS

| | | | |
|---|---|---|---|
| 1691871 | 11/1991 | U.S.S.R. | 434/271 |
| 732843 | 6/1955 | United Kingdom | 434/271 |

*Primary Examiner*—Jeffrey A. Smith
*Attorney, Agent, or Firm*—Paul S. Clohan

[57] ABSTRACT

A training device for digital assessment of intraocular pressure (IOP) that includes a body, top, bottom cover, and two legs. The body contains ten cylindrical cavities, the depth of each cavity selected such that the sloped bottom of the cavity intersects with a 0.625-inch diameter hole that is drilled into the body from the top. A thin, circular piece of latex membrane approximately one-inch in diameter is located directly over each 0.625-inch diameter hole. The bottom contains ten tapped holes, the centers of which are aligned with the centers of the cavities, each containing a threaded rod with sufficient length to permit the rod to be rotated up to move a plastic plunger sized so as to easily slide into and out of its cavity in the body without binding. Moving the rotated position of the threaded rod with respect to the bottom determines the location of the plastic plunger in the cavity. Pressurization of each latex membrane surface occurs when a spherical latex bladder containing a non-compressible liquid is inserted inside each cavity. Prior to use by the trainee, the pressure in each liquid-filled bladder is established by adjusting the position of the plunger with the threaded rod while monitoring IOP with a Schiotz tonometer. The IOP of each of the ten membranes may then be established in various configurations depending upon the objective of the training session, e.g., set from 5 mm Hg to 50 mm Hg, increasing in 5 mm increments. As the training progresses, the ten samples can be calibrated in a random fashion in order to ascertain how well the previously trained health care professional can digitally measure IOP.

10 Claims, 3 Drawing Sheets

5,868,580

TRAINING DEVICE FOR DIGITAL ASSESSMENT OF INTRAOCULAR PRESSURE

CROSS-REFERENCE TO RELATED APPLICATIONS

Not Applicable.

STATEMENT REGARDING FEDERALLY SPONSORED RESEARCH OR DEVELOPMENT

Not Applicable.

BACKGROUND OF THE INVENTION

Intraocular Pressure (IOP) is an extremely important characteristic of a physical state of the eye, especially in glaucoma patents. Nearly one percent of the total population of the United States suffers from this form of blindness. Glaucoma is characterized by an increase in IOP which causes visual defects and ultimately may cause irreversible blindness. As the IOP rises to abnormal levels, damage is caused to the ocular nerve and surrounding retinal tissues. The patient seldom experiences any symptoms that might indicate that the disease exists until major damage occurs.

As part of many standard eye examinations, a test of IOP known as tonometry is performed to detect the early stages of glaucoma. Tonometry broadly relates to the measurement of tension in living tissue and has special meaning in ophthalmology relating to IOP and the health of the eye. Pressure in the eye is not measured directly, but is typically inferred by measuring the eye's response to pressure exerted upon the cornea.

A measure of the pressure within the eye is conventionally obtained by indenting to a given depth or flattening to a given extent a portion of a measurement surface of the eye, usually the cornea, and then determining the amount of force required to produce the given flattening or indentation. The flattening or indentation is resisted by the resiliency of the measurement surface and by the internal pressure of the eyeball. The determined force is then converted to a measurement of IOP.

In some occasions, health care professionals are required to assess IOP digitally (i.e., with their fingertip). The ability to digitally determine IOP is critical in trauma cases where time is of the essence and proper measuring devices may not be available. Additionally, measuring devices may not be available in some locations. It has been proven that a minimal amount of training allows a health care professional to accurately assess IOP digitally. In the past, this type of training has been done on cadaveric human or animal eyes which has many drawbacks, among them being the problems associated with obtaining and maintaining human or animal tissue over long periods of time and to eliminate any possibility of disease transmission from contaminated samples.

BRIEF SUMMARY OF THE INVENTION

It is therefore an object of the present invention to provide an easily calibrated, reliable, and repeatable training device for determining IOP that does not use cadaveric eyes.

A further object of the present invention is to provide an IOP training device that is easily calibrated without the necessity for external fluid filled syringes or infusion cannulas.

Still other objects and advantages of the present invention will become readily apparent to those skilled in this art from the detailed description, wherein only the preferred embodiment of the present invention is shown and described, simply by way of illustration of the best mode contemplated of carrying out the present invention. As will be realized, the present invention is capable of other and different embodiments, and its several details are capable of modifications in various obvious respects, all without departing from the present invention. Accordingly, the drawings and descriptions are to be regarded as illustrative in nature, and not as restrictive.

These and other objects are achieved by a training device for digital assessment of intraocular pressure that includes a body, top, bottom cover, and two legs. The legs are designed such that the device can be set on a table. The body contains ten cylindrical cavities, with each cavity being one-inch in diameter. The depth of each cavity is selected such that the sloped bottom of the one-inch cavity intersects with a 0.625-inch diameter hole that is drilled into the body from the top. The ten holes in the top have a countersink to provide a tapered circular opening in the top. The top is attached to the body by a series of machine screws that are threaded into mating threaded holes in the body. Screws are located concentrically around each cavity so as to provide a tight seal between the two flat surfaces. A thin, circular piece of latex membrane approximately one-inch in diameter, with a thickness of 0.005 inches is located directly over each 0.625-inch diameter hole. Each membrane is tightly pressed into place between the body and the top as the screws are tightened to fasten the top to the body.

The bottom is attached to the body with a series of machine screws that are threaded into mating threaded holes in the body. These screws are located concentrically around each cavity to provide a tight seal between the two flat surfaces. The bottom contains ten tapped holes, the centers of which are aligned with the centers of the cavities. Threaded into each tapped hole is a threaded rod with sufficient length to permit the threaded rod to be rotated up into the cavity to cause a plastic plunger, containing another cylindrical cavity sized to accept the threaded rod to move longitudinally into or out of this cavity. A hexagonal nut is threaded onto the rod prior to threading the rod into the bottom. Each threaded rod may then be locked into place by rotating a nut clockwise, while preventing the rotation of the threaded rod until the nut jams against the bottom. A plastic plunger is sized so as to easily slide into and out of the cavity in the body without binding. The rotated position of the threaded rod with respect to the bottom determines the location of the plastic plunger in the cavity. Gravity, plus the internal pressure of the liquid-filled bladder, causes the plastic plunger to return to the vicinity of the bottom of the cylindrical cavity as the threaded rod is turned counterclockwise to cause the threaded rod to move longitudinally out of its cylindrical cavity.

Pressurization of each latex membrane surface occurs in the following manner. A spherical latex bladder with a diameter of approximately 0.78-inches is inserted inside each cavity. Each bladder contains approximately 0.132-ounces of a non-compressible liquid. Each bladder can be fabricated using latex material with a thickness of 0.005-inches. Care must be taken to exclude all air from the bladder. The exact quantity of liquid contained in each bladder is not critical, since the liquid is compressed by the plastic plunger as the threaded rod is rotated clockwise. However, the volume of liquid must be sufficient to achieve the desired pressure when the pressure adjusting plunger is situated centrally in the cavity. Excessive liquid in the bladder makes it difficult to reduce the internal pressure to the desired level when the plunger is in its minimum pressure position.

Prior to use by the trainee, the pressure in each liquid-filled bladder is established by adjusting the position of the plunger with the threaded rod while monitoring IOP with a Schiotz tonometer, that had been previously calibrated to the flexible membrane surface. The IOP of each of the ten membranes may then be established in various configurations depending upon the objective of the training session. Initially, the training should be used to expose the trainee to precisely calibrated samples, whose IOP's increase by known increments, such as 5 mm Hg. Thus, the ten samples contained in the training device would be set from 5 mm Hg to 50 mm Hg, increasing in 5 mm increments. As the training progresses, a validation phase would be entered where the ten samples are calibrated in a random fashion in order to ascertain how well the previously trained health care professional can digitally measure IOP.

DETAILED DESCRIPTION OF THE INVENTION

It has been proven that a minimal amount of training allows a health care professional to accurately assess IOP digitally. For example, at the 1996 annual meeting of the Association for Research in Vision and Ophthalmology, a poster session was presented by C. D. Bimbach and M. M. Leen indicating digital assessment of IOP can be accurate and reliable when the provider is adequately trained. For their study, cadaveric human eyes were pressurized using a needle through the optic nerve stump. IOP's ranging from 5 mm to 40 mm Hg were established using Schiotz tonometry. Their study indicated that experienced glaucoma specialists were correct to within 1 mm Hg 46% of the time and within 5 mm Hg 100% of the time. Less experienced third year ophthalmology residents were correct to within 1 mm Hg 21% of the time, within 5 mm Hg 54% of the time, within 10 mm Hg 88% of the time, and within 15 mm Hg 100% of the time. Typically, IOP is approximately 20 mm Hg in healthy eyes, and may rise to more than 40 mm Hg in diseased eyes.

Figure 1:
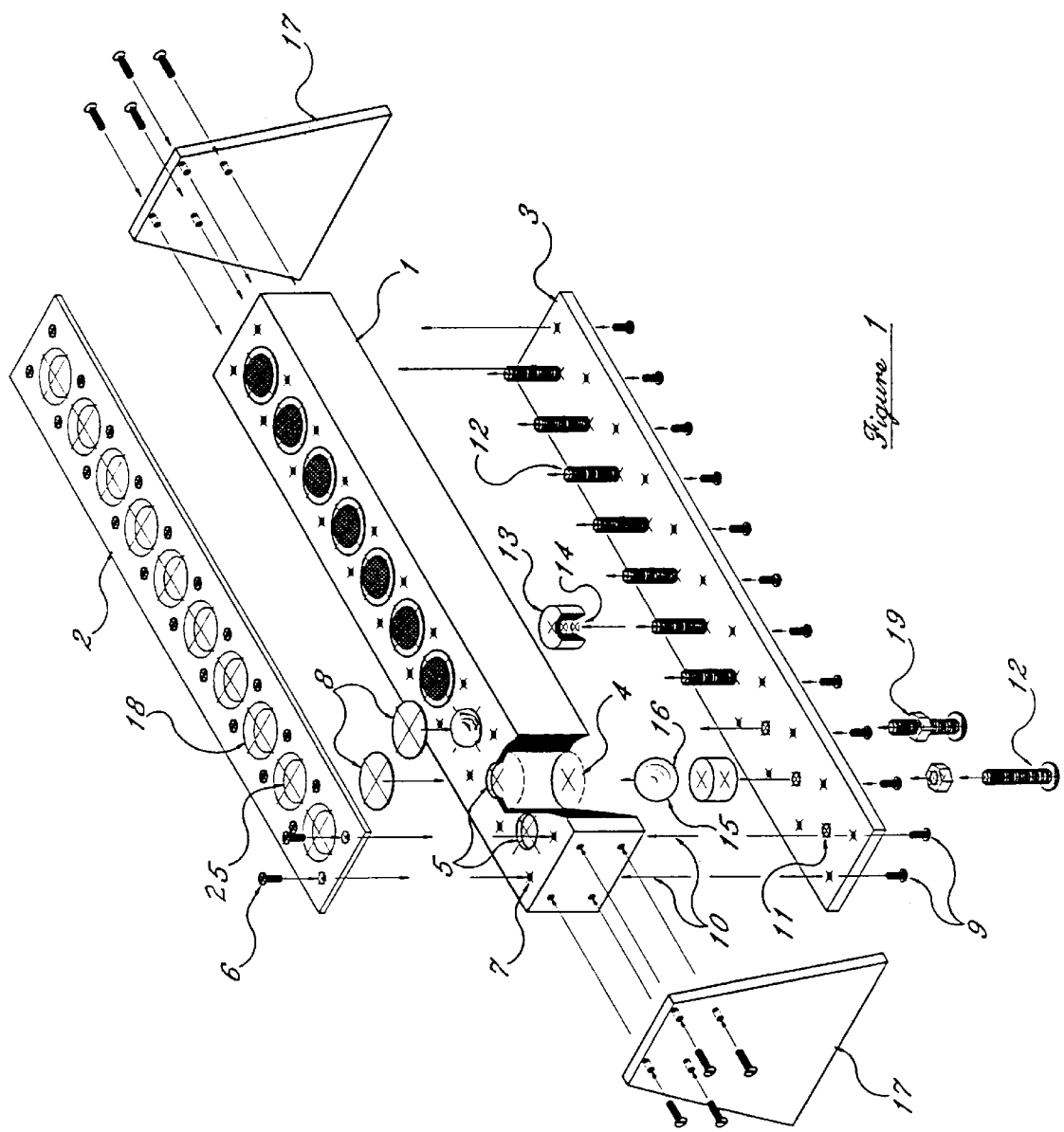
FIG. 1 is an exploded perspective view of the preferred embodiment of the invention.

FIG. 1 shows an exploded view of the preferred embodiment of the invention. The device includes body 1, top 2, bottom cover 3, and two legs 17. These members may be made from plastic or other suitable material. Legs 17 are designed such that the device can set on a table. Body 1 contains ten cylindrical cavities 4, with each cavity 4 being one-inch or 25 mm in diameter. Each cavity 4 can be formed by drilling into body 1 from the bottom of body 1 with a one-inch drill bit having a point angle of 118 degrees forming a 118 degree angle at the bottom of cavity 4. The depth of each cavity 4 is selected such that the sloped bottom of the one-inch cavity 4 intersects with a 0.625-inch or 16 mm diameter hole 5 that is drilled into body 1 from the top. Holes 25 in top 2 have a countersink 18 to provide a tapered circular opening in top 2. Top 2 is attached to body 1 by a series of machine screws 6 that are threaded into mating threaded holes 7 in body 1. Screws 6 are located concentrically around each cavity 4 so as to provide a tight seal between the two flat surfaces. During assembly, a thin, circular piece of latex membrane 8 approximately one-inch in diameter, with a thickness of 0.005 inches or 0.127 mm, similar to that typically found in surgical gloves, is located directly over each 0.625-inch diameter hole 5. Each membrane 8 is tightly pressed into place between body 1 and top 2 as screws 6 are tightened to fasten top 2 to body 1.

Bottom 3 is attached to body 1 with a series of machine screws 9 that are threaded into mating threaded holes 10 in body 1. These screws 9 are located concentrically around each cavity 4 so as to provide a tight seal between the two flat surfaces. Bottom 3 contained ten tapped holes 11, the centers of which are aligned with the centers of cavities 4. Threaded into each tapped hole 11 is a threaded rod 12 with sufficient length to permit threaded rod 12 to be rotated up into cavity 4 to cause a plastic plunger 13, containing a cylindrical cavity 14 sized to accept threaded rod 12 to move longitudinally into or out of cylindrical cavity 14. A hexagonal nut 19 is threaded onto rod 12 prior to threading rod 12 into bottom 3. Each threaded rod 12 may then be locked into place by rotating nut 19 clockwise, while preventing rotation of threaded rod 12 until nut 19 jams against bottom 3. Plastic plunger 13 is sized so as to easily slide into and out of cavity 4 in body 1 without binding. The rotated position of threaded rod 12 with respect to bottom 3 determines the location of plastic plunger 13 in cavity 4. Gravity, plus the internal pressure of liquid-filled bladder 15, causes plastic plunger 13 to return to the vicinity of the bottom of cylindrical cavity 14 as threaded rod 12 is turned counterclockwise to cause threaded rod 12 to move longitudinally out of cylindrical cavity 14.

Pressurization of each latex membrane 8 surface occurs in the following manner. A spherical latex bladder 15 with a diameter of approximately 0.78-inches or 20 mm is inserted inside each cavity 4. Each bladder contains approximately 0.132-ounces or 4 ml of a non-compressible liquid such as saline solution, silicon, or sterile water. Each bladder 15 can be fabricated using latex material with a thickness of 0.005-inches or 0.127 mm, similar to that found in surgical gloves. One method of fabricating the sealed, liquid-filled bladder 15 is by using a finger of a surgical glove. Another method would be to construct the bladder entirely from a low viscosity gel such as NORSIL RTV 919. After placing the non-compressible liquid in the open ended reservoir, a knot 16 is tied in the latex material, thereby trapping the liquid in bladder 15. Care must be taken to exclude all air from bladder 15. The exact quantity of liquid contained in each bladder 15 is not critical, since the liquid is compressed by plastic plunger 13 as threaded rod 12 is rotated clockwise. However, the volume of liquid must be sufficient to achieve the desired pressure when the pressure adjusting plunger 13 is situated centrally in cavity 4. Excessive liquid in bladder 15 makes it difficult to reduce the internal pressure to the desired level when plunger 13 is in its minimum pressure position.

Figure 2:
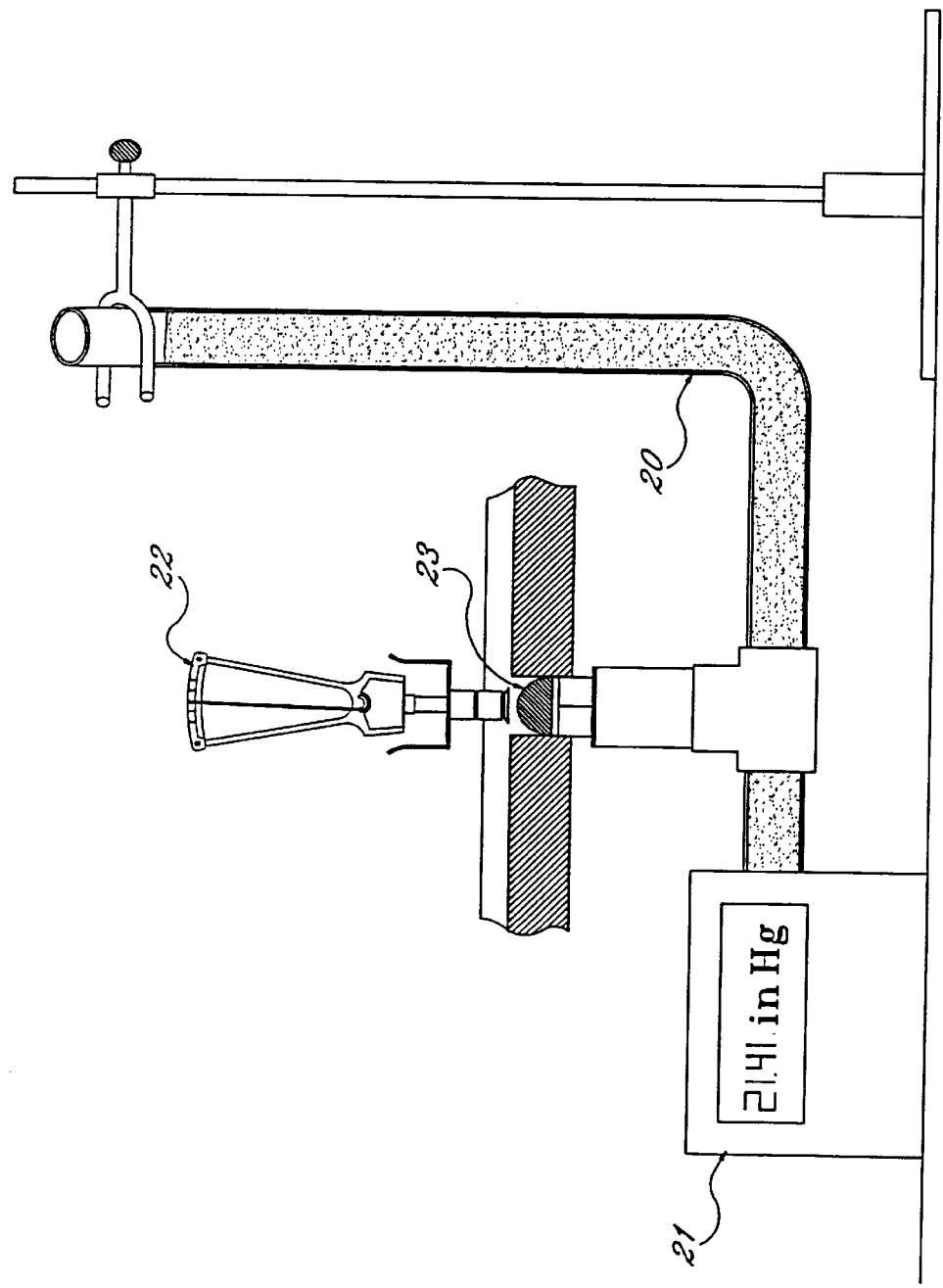
FIG. 2 depicts the calibration of the present invention using a Schiotz Tonometer.

FIG. 2 shows one method of calibration of the device. Prior to use by the trainee, the pressure in each liquid-filled bladder 15 is established by adjusting the position of plunger 13 with threaded rod 12 while monitoring IOP with Schiotz tonometer 22, that had been previously calibrated to flexible membrane surface 8. The IOP of each of the ten membranes 8 may be established in various configurations depending upon the objective of the training session. Initially, the training should be used to expose the trainee to precisely calibrated samples, whose IOP's increase by known increments, such as 5 mm Hg. Thus, the ten samples contained in the training device would be set from 5 mm Hg to 50 mm Hg, increasing in 5 mm increments. As the training progresses, a validation phase would be entered where the ten samples are calibrated in a random fashion in order to ascertain how well the previously trained health care professional can digitally measure IOP.

Figure 3:
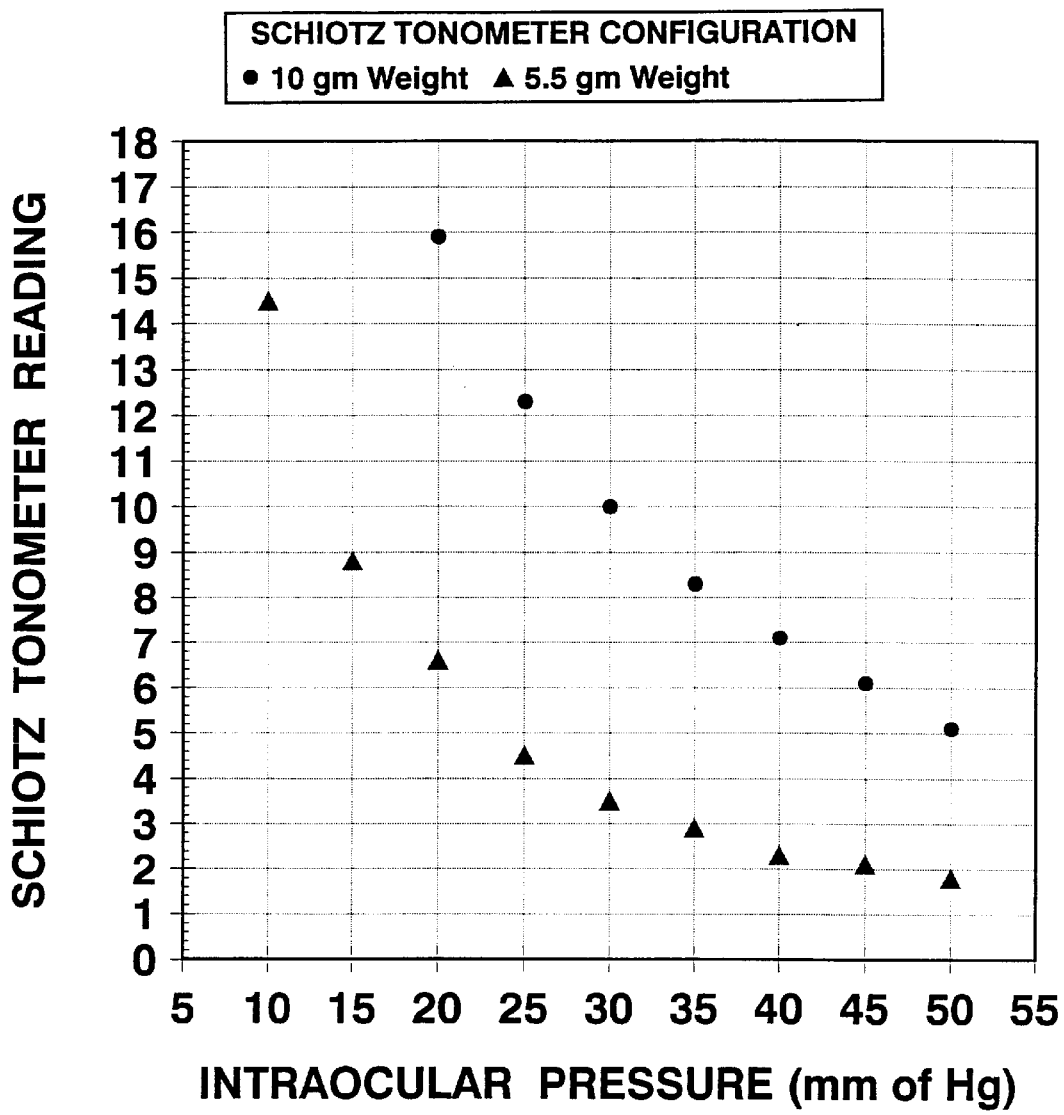
FIG. 3 is a graph of the calibration of the present invention.

As shown in FIG. 2, Schiotz tonometer 22 used to adjust pressurized bladders 15 of the training device is calibrated to the latex material by pressurizing latex reservoir 23, fabricated using latex material with a thickness of 0.005-inches or 0.127 mm, held captive within cylindrical cavity 4. Reservoir 23 is sized to replicate spherical latex bladder 15. It has a diameter of approximately 0.78-inches or 20 mm. Reservoir 23 was pressurized by a column of water 20 while monitoring the hydrostatic pressure with digital pressure indicator 21. As the elevation of the column of water 20 was increased above the elevation of reservoir 23, the internal pressure of reservoir 23 increased. A series of measurement was taken at each data point. This calibration of Schiotz tonometer 23 is necessary because the flexible membrane material used the training device has slightly different deflection characteristics than the human eye at various internal pressures. Table I below shows the calibration data for Schiotz tonometer 22 and FIG. 3 shows the calibration curve for this data.

TABLE I

| INTRAOCULAR PRESSURE mm Hg | SCHIOTZ READING 5.5 gm Weight | SCHIOTZ READING 10 gm Weight |
|---|---|---|
| 10 | 14.5 | |
| 15 | 8.8 | |
| 20 | 6.6 | 15.9 |
| 25 | 4.5 | 12.3 |
| 30 | 3.5 | 10.0 |
| 35 | 2.9 | 8.3 |
| 40 | 2.3 | 7.1 |
| 45 | 2.1 | 6.1 |
| 50 | 1.8 | 5.1 |

It will be readily seen by one of ordinary skill in the art that the present invention fulfills all of the objects set forth above. After reading the foregoing specification, one of ordinary skill will be able to effect various changes, substitutions of equivalents and various other aspects of the present invention as broadly disclosed herein. It is therefore intended that the protection granted hereon be limited only by the definition contained in the appended claims and equivalents thereof.

Having thus shown and described what is at present considered to be the preferred embodiment of the present invention, it should be noted that the same has been made by way of illustration and not limitation. Accordingly, all modifications, alterations and changes coming within the spirit and scope of the present invention are herein meant to be included.

We claim:

1. A training device for digital assessment of intraocular pressure in humans comprising:

a housing having a plurality of cavities therein;

said plurality of cavities each having a simulated human eyeball therein; and means for providing an intraocular pressure within each said simulated human eyeball;

wherein said means for providing an intraocular pressure is independently adjustable to provide an identical pressure or a random pressure in each simulated human eyeball.

2. The device of claim 1 wherein said simulated eyeball comprises a liquid filled bladder.

3. The device of claim 2 wherein said liquid filled bladder is spherical in shape.

4. The device of claim 2 wherein said liquid is saline.

5. The device of claim 2 wherein said liquid is silicon.

6. The device of claim 2 wherein said means for providing an independently adjustable intraocular pressure within each said simulated eyeball comprises a plunger for compressing each said simulated human eyeball within each said cavity.

7. The device of claim 6 wherein said plunger uses a rod threaded into said housing to adjust the position of said plunger.

8. The device of claim 7 wherein said plunger is pivotally mounted to said rod.

9. The device of claim 1 wherein said simulated human eyeball comprises a low viscosity silicon gel.

10. The device of claim 9 wherein said means for providing an independently adjustable intraocular pressure comprises a plunger for compressing said silicon gel.

* * * * *